United States Patent [19]

Varouxis

[11] Patent Number: 5,385,059
[45] Date of Patent: Jan. 31, 1995

[54] SLUDGE SAMPLER

[76] Inventor: Theodore Varouxis, 814 N. Henry St., Alexandria, Va. 22314

[21] Appl. No.: 22,903

[22] Filed: Feb. 26, 1993

[51] Int. Cl.⁶ .................... E21B 49/02; E21B 49/08
[52] U.S. Cl. ................ 73/864.66; 73/864.45; 73/864.63; 33/717; 175/20
[58] Field of Search ........... 73/864.63, 864.66, 864.44, 73/864.45; 175/20, 58, 59; 33/717, 718

[56] References Cited

U.S. PATENT DOCUMENTS

| | | | |
|---|---|---|---|
| 1,759,444 | 5/1930 | Dunn et al. | 73/864.66 X |
| 2,274,869 | 3/1942 | Pfeiffer | 73/864.66 X |
| 2,302,884 | 11/1942 | O'Neill | 73/864.66 |
| 2,436,737 | 2/1948 | White et al. | 73/864.66 X |
| 2,598,183 | 5/1952 | Long et al. | 73/864.66 |
| 2,650,499 | 9/1953 | Quist | 73/864.66 |
| 2,654,251 | 10/1953 | Harrington | 73/864.66 |
| 2,998,726 | 9/1961 | Peterson | 73/864.66 |
| 3,318,394 | 5/1967 | Gleason, Jr. et al. | 73/864.44 X |
| 3,497,018 | 2/1970 | Shultz et al. | 175/20 X |
| 3,576,220 | 4/1971 | Gill | 175/20 X |
| 3,623,369 | 11/1971 | Kejellberg | 73/864.66 X |
| 3,826,144 | 7/1974 | Wessels | 73/864.63 X |
| 4,157,664 | 6/1979 | Robinson | 73/864.66 X |
| 4,821,587 | 4/1989 | Rogers | 73/864.66 X |
| 4,869,118 | 9/1989 | Keller | 73/864.63 |
| 4,888,999 | 12/1989 | Kozak | 73/864.44 X |

Primary Examiner—Thomas P. Noland
Attorney, Agent, or Firm—James Creighton Wray

[57] ABSTRACT

A sludge sampler for industrial settling ponds has a handle and an insertion tube of known graduated length so that the sampler may be embedded in sludge at a known depth. At the bottom of the insertion tube is a frame which holds a sampler container jar and which terminates downwardly in a thin walled insertion cone. A lever at the top slides a rod and lifts a cap on the jar so that free flowing sludge may fill the jar. The jar is held in a cage pivoted on the frame. The center of the cover and one edge of the cage are connected by pivoted links. As the cover is lifted, the cage is tipped, tipping the jar to receive the sludge. As the lever is returned to its closed position, the jar-capturing cage is returned to its upright position, the cover is lowered, the jar is covered before the insertion tube is lifted and the cage, the frame, the cone and the jar are lifted out of the sludge.

8 Claims, 4 Drawing Sheets

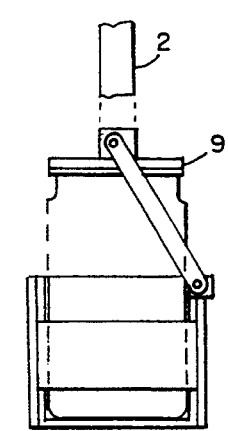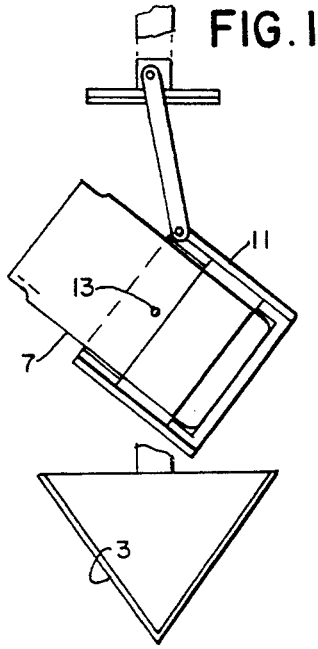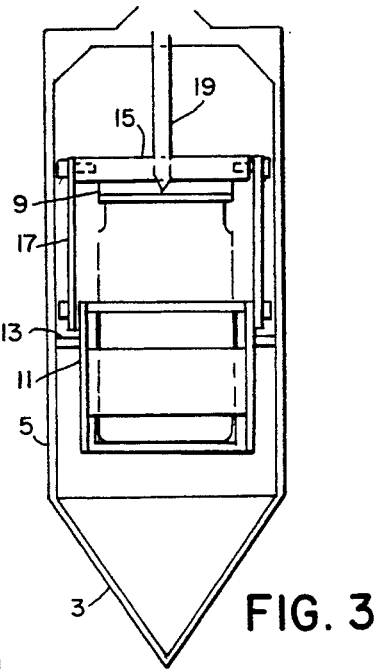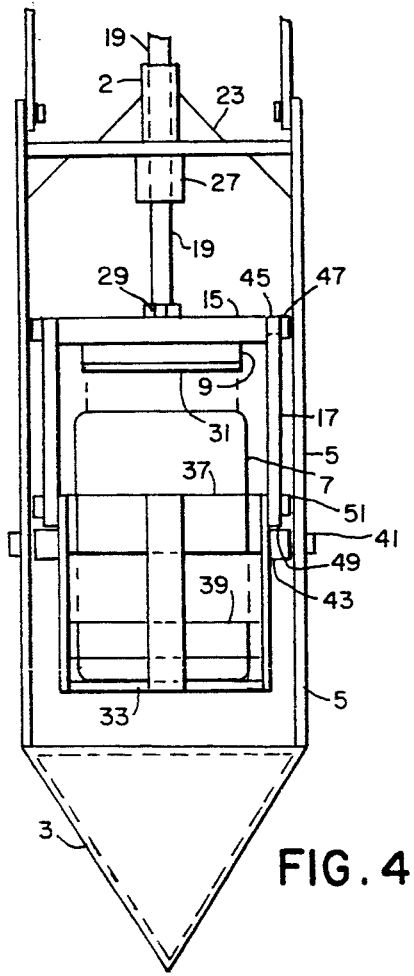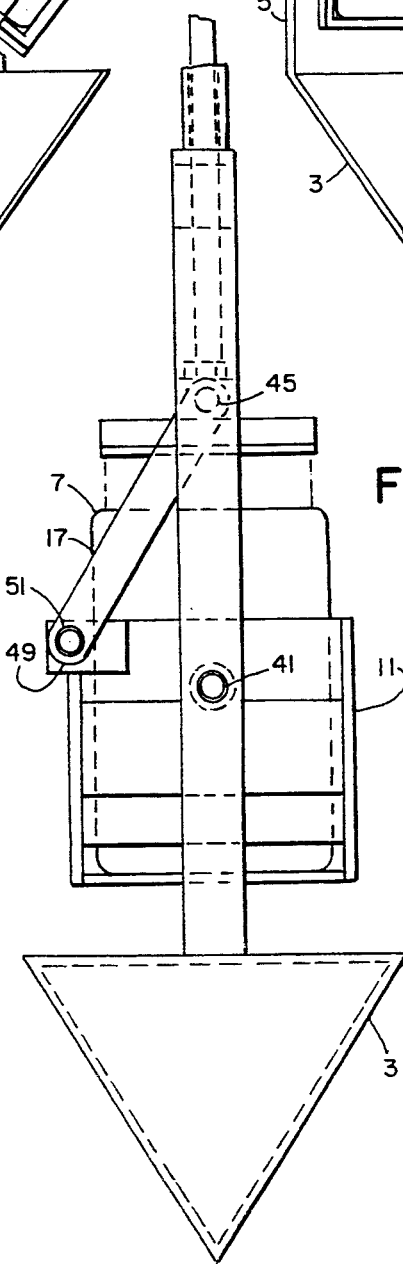
FIG. 1
FIG. 2
FIG. 3
FIG. 4
FIG. 5

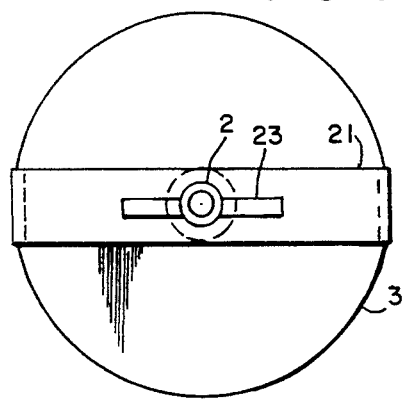
FIG. 9
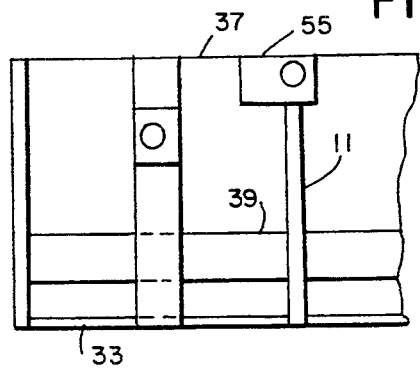
FIG. 10
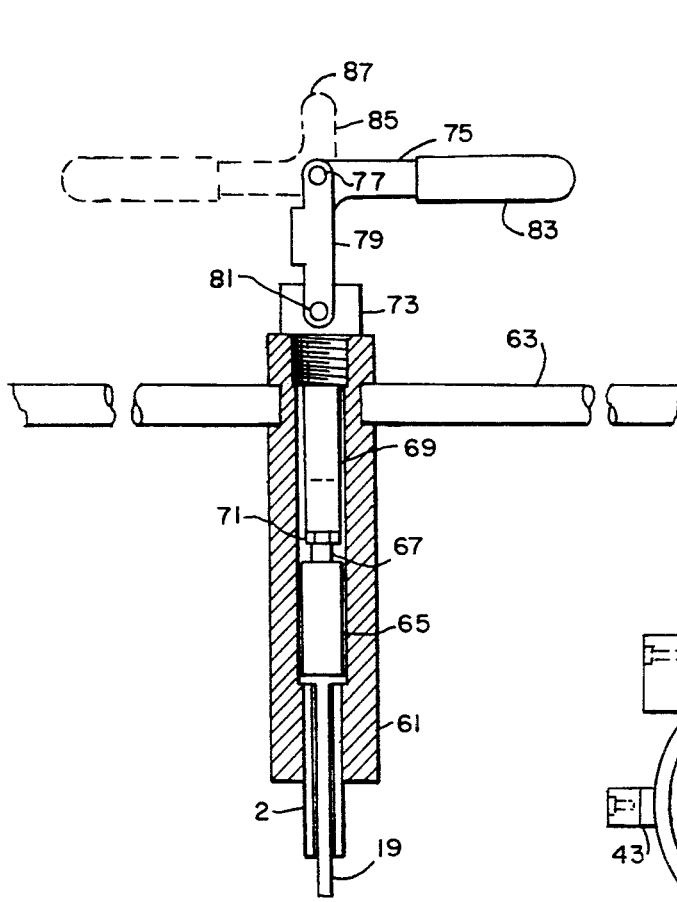
FIG. 11
FIG. 13
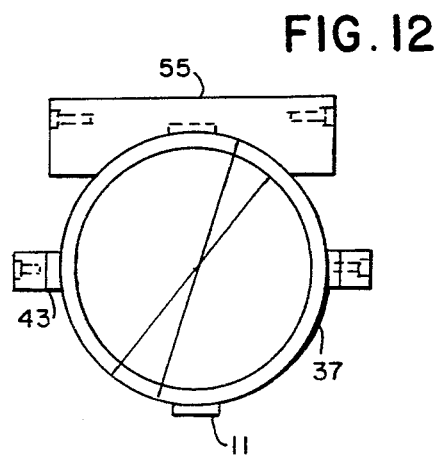
FIG. 12

SLUDGE SAMPLER

BACKGROUND OF THE INVENTION

Settling ponds require periodic sampling of sludge at the bottom of the ponds to determine the nature and content of the sludge. Sludge samples must be taken at different depths. Some sludge is fluid and easily flows. Other sludge is thick and is difficult to flow.

A need exists for a sludge sampler which can be used in all types of sludge and which is easily insertable into the sludge and which promotes the flow of sludge into the sampler so that the sample may be removed and analyzed.

SUMMARY OF THE INVENTION

The present invention fulfills that need by providing a sludge sampler in which the sample container is tipped to present the entire open end of the container to the sludge and to encourage the sludge to flow into the container, without requiring the sludge to flow around the top of the container and between elements of the sampler.

A sludge sampler for industrial settling ponds has a handle and an insertion tube of known graduated length so that the sampler may be embedded in sludge at a known depth. At the bottom of the insertion tube is a frame which holds a sampler container jar and which terminates downwardly in a thin walled insertion cone. A lever at the top slides a rod and lifts a cap on the jar so that free flowing sludge may fill the jar. The jar is held in a cage pivoted on the frame. The center of the cover and one edge of the cage are connected by pivoted links. As the cover is lifted, the cage is tipped, tipping the jar to receive the sludge. As the lever is returned to its closed position, the jar-capturing cage is returned to its upright position, the cover is lowered, the jar is covered before the insertion tube is lifted and the cage, the frame, the cone and the jar are lifted out of the sludge.

A sludge sampler apparatus has an insertion pipe having markings for indicating length and depth. A frame is connected to a bottom end of the pipe. An insertion cone is connected to a bottom of the frame. A container is mounted in the frame between the cone and the bottom end of the pipe. A rod is mounted for sliding in the pipe. A bottom end of the rod extends below the bottom end of the pipe. A stopper is connected to the bottom end of the rod for opening and closing the container. A handle is connected to a top of the pipe. A lifter is connected to a top of the rod for lifting the rod and the stopper. A clamp is connected to the top of the rod for holding the rod and the stopper downward.

A pivot is connected between the container and the frame for tipping and aligning the container with the frame.

A link has first and second ends. A first pin connects the first end of the link and the stopper, and a second pin connects the second end of the link and the container for moving the container about the pivot as the stopper is raised and lowered by the rod.

A cage surrounds the container for holding the container.

The cage comprises spaced hoops and a floor and parallel straps connected to the hoops.

First and second pivots are connected to the cage and to the frame for pivoting the cage on the frame.

The frame has a horizontal arm having a center connected to the bottom of the pipe with a hole through the arm for the rod. The arm has first and second opposite ends and first and second vertical members. The vertical members have upper ends connected respectively to the opposite ends of the horizontal arm, and lower ends connected to the insertion cone. The first and second pivots are connected to the first and second vertical members, respectively.

A bar is connected to the bottom of the rod beneath the horizontal arm. A round stopper is connected to a bottom of the bar for sealing the container. First and second links have first pins which connect first ends of the first and second links to opposite first and second ends of the bar. The first and second pins connect second ends of the first and second links to spaced connections on the cage at positions on the cage spaced from the pivots, for pulling on the links and tilting the cage about the pivots when the stopper is lifted from the container, and for repositioning the cage by pushing on the links when the stopper is lowered on the container.

These and further and other objects and features of the invention are apparent in the disclosure, which includes the above and ongoing written specification, with the claims and the drawings.

BRIEF DESCRIPTION OF THE DRAWINGS

FIG. 1 is a side view of the invention.

FIG. 2 is a side view of the invention with the jar closed.

FIG. 3 is a front view of the invention.

FIG. 4 is a front view of the invention showing details of the frame and stopper.

FIG. 5 is a side view of the invention showing details of the frame and stopper.

FIG. 9 is a top view of the frame and cone.

FIG. 10 is a side view of the bottle cage.

FIG. 11 is a front view of the bottle cage.

FIG. 12 is a top view of the bottle cage.

FIG. 13 is a sectional view of the handle and clamp.

DETAILED DESCRIPTION OF THE DRAWINGS

Figure 6:
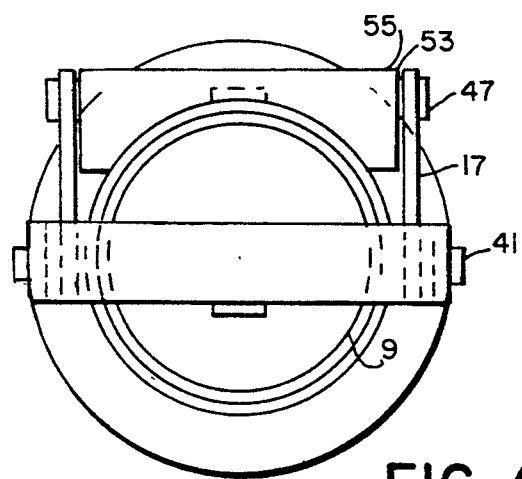
FIG. 6 is a top view of the invention.
Figure 8:
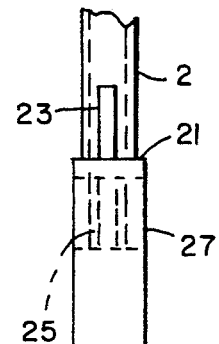
FIG. 8 is a side view of the frame and cone.
Figure 7:
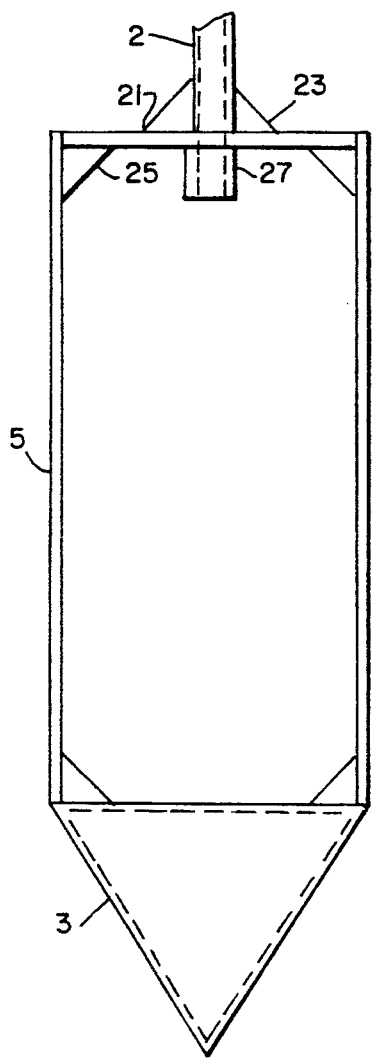
FIG. 7 is a front view of the frame and cone.

The container end of the sampler is generally referred to by the numeral 1 in FIGS. 1, 2 and 3. A pipe 2 lowers the sampler into position in a bed of sludge. A cone 3 at the bottom of a frame 5 helps the sampler to penetrate the sludge bed as the pipe, sampler and cone are lowered. A container 7 is sealed by a stopper 9, which is removed so that the sludge may flow into the container. The container is held in a cage 11 which surrounds a lower portion of the container, and the cage is pivoted to the frame 5 by pivots 13. A bar 15 extends across the stopper 9, and links 17 connect the ends of the bar 15 to the cage 11. As a rod 19 is raised to lift the stopper 19 the links 17 are pulled upward, causing the cage 11 to rotate on pivots 13, presenting the full open end of the container 7 to the sludge, as shown in FIG. 1.

As shown in the details of FIGS. 4, 5 and 6, the sludge sampler 1 has hollow cone penetrator 3 which is completely closed. Two parallel stainless steel frame members 5 connect the top of the penetrator cone 3 to a cross member 21, which is connected to the bottom of pipe 2 and which is supported on the bottom of the pipe by gussets 23. Gussets 25 interconnect the top frame member 21 and the parallel rigid frame sides 5. Preferably the penetrator cone and frame 5 are made of stainless steel. A cylinder 27 is welded beneath the horizontal frame member 21 in continuation of the pipe 2 to guide the sliding rod 19. The bottom of rod 19 is threaded and screwed into a central tapped hole in the bar 15. A lock nut 29 holds the assembly together.

A gasket 31 made of a disc of Viton is secured to the bottom of stopper 9. The stopper is a round plate secured to the bottom of bar 15.

The container 7 is a strong laboratory bottle with a large open mouth. The bottle is held in a cage 11, which is made up of a floor 33, four stainless steel bar strap side members 35, and upper and lower stainless steel hoops 37 and 39, which are all welded together at intersections.

Two of the opposite side members 35 receive pivot pins 41, which extend through vertical frame members 5 and into the side members 35 of the cage 11. The spacing of the cage and the frame members 5 is maintained by thick washers 43.

Links 17 have first upper ends 45, which have holes to receive first pins 47. The pins 47 are secured in opposite ends of the bar 15. Lower ends 49 of the links 17 have openings which receive second pivot pins 51, which are held in outer ends 53 of a cross bar 55, which is connected to the upper hoop 37.

After the sampler 1 has been inserted into the sludge by pushing the cone 3, frame 5 and container 7 into the sludge using pipe 2, the rod 19 is lifted, raising the stopper 9 and gasket 31 and pulling the links 17, which tips the cage 11 and the container 7, exposing the open end of the container into the sludge.

At the top of the pipe 2 is mounted a handle housing 61. Handles 63 extend outward from the top of the handle housing for about 1 ft. At the top of control rod 19, a spring-loaded plunger 65 is mounted. The plunger is connected to a rod 67, which slides in the plunger to compress a spring to hold the rod 19 and the stopper 9 downward with a predetermined force. An adjustable extension 69 is connected to the top of the rod 67, and a lock nut 71 ensures that the adjustment is held.

A Destaco toggle clamp has a base 73 which is threaded into the top of the opening in the handle housing 61. A leather 75 is pivoted on pin 77 and link 79, which is connected to the pin 81 in the clamp base 73. Lever 75 has a hand grip 83 and an activating arm 85, with a toe 87 which presses downward on the upper end of sliding actuator rod 69. When the lever 75 is in the right hand position, the top end of actuator rod 69 is forced downwardly, forcing rod 67 to compress the spring in the plunger 65, pressing rod 19 and stopper 9 downward. When the lever is moved to the left hand position, the toe 87 is released from the top of the rod 69, and the spring-loaded plunger 65 lifts the rod 19 and lifts the stopper 9 and the connected link 17 to open and tilt the collection bottle 7. The handle housing handle, lever and spring-loaded plunger are particularly shown with reference to FIG. 13.

Figure 14:
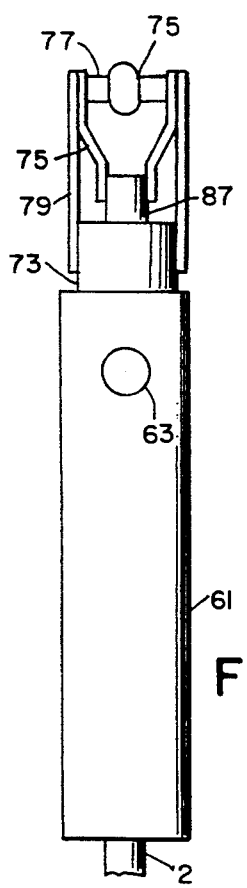
FIG. 14 is a side view of the handle and clamp.
Figure 16:
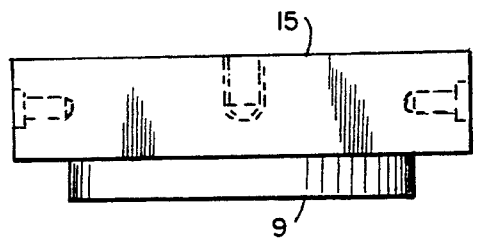
FIG. 16 is a front view of the bottle stopper.
Figure 15:
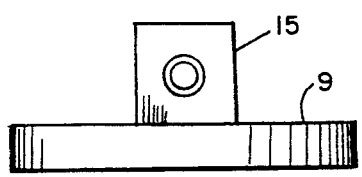
FIG. 15 is a side view of the bottle stopper.
Figure 17:
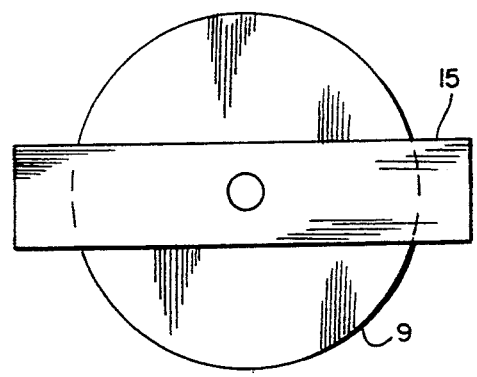
FIG. 17 is a top view of the bottle stopper.
Figure 18:
FIG. 18 is a side view of a link.

FIG. 14 is a side elevation of the elements shown in FIG. 13.

While the invention has been described with reference to specific embodiments, modifications and variations of the invention may be constructed without departing from the scope of the invention, which is defined in the following claims.

I claim:

1. A sludge sampler apparatus comprising an insertion pipe having markings for indicating length and depth, a frame connected to a bottom end of the pipe, an insertion cone connected to a bottom of the frame, a container tiltably mounted in the frame between the cone and the bottom end of the pipe, a rod mounted for sliding in the pipe, a bottom end of the rod extending below the bottom end of the pipe, a stopper connected to the bottom end of the rod for opening and closing a top of the container, a handle connected to a top of the pipe, a lifter connected to a top of the rod for lifting the rod and the stopper, and a clamp connected to the top of the rod for holding the rod and the stopper downward.

2. The apparatus of claim 1, further comprising a pivot connected between the container and the frame for tipping and aligning the container with the frame.

3. The apparatus of claim 2, further comprising a link having first and second ends, a first pin connecting the first end of the link and the stopper, and a second pin connecting the second end of the link and the container for moving the container about the pivot as the stopper is raised and lowered by the rod.

4. The apparatus of claim 1, further comprising a cage surrounding the container for holding the container.

5. The apparatus of claim 4, wherein the cage comprises spaced hoops and a floor and parallel straps connected to the hoops.

6. The apparatus of claim 5, further comprising first and second pivots connected to the cage and connected to the frame for pivoting the cage on the frame.

7. The apparatus of claim 6, wherein the frame comprises a horizontal arm having a center connected to the bottom of the pipe with a hole through the arm for the rod, and having first and second opposite ends and first and second vertical members, the vertical members having upper ends connected respectively to the opposite ends of the horizontal arm and having lower ends connected to the insertion cone, the first and second pivots being connected to the first and second vertical members, respectively.

8. The apparatus of claim 7, further comprising a bar connected to the bottom of the rod beneath the horizontal arm, a round stopper connected to a bottom of the bar for sealing the container, first and second links having first pins connecting first ends of the first and second links to opposite first and second ends of the bar, first and second pins connecting second ends of the first and second links to spaced connections on the cage at positions on the cage spaced from the pivots for pulling on the links and tilting the cage about the pivots when the stopper is lifted from the container, and for repositioning the cage by pushing on the links when the stopper is lowered on the container.

* * * * *